（12) United States Patent
Tonini

(10) Patent No.: US 8,457,731 B2
(45) Date of Patent: Jun. 4, 2013

(54) METHOD FOR ASSESSING ANESTHETIZATION

(75) Inventor: Giulio Tonini, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 477 days.

(21) Appl. No.: 12/658,873

(22) Filed: Feb. 16, 2010

(65) Prior Publication Data

US 2010/0210963 A1 Aug. 19, 2010

Related U.S. Application Data

(60) Provisional application No. 61/152,880, filed on Feb. 16, 2009.

(51) Int. Cl.
*A61B 5/04* (2006.01)
(52) U.S. Cl.
USPC .......................................................... 600/544
(58) Field of Classification Search
USPC ................................................ 600/544, 545
See application file for complete search history.

(56) References Cited

U.S. PATENT DOCUMENTS

| 2002/0173729 A1* | 11/2002 | Viertio-Oja et al. | 600/544 |
| 2005/0014834 A1* | 1/2005 | Reynolds et al. | 514/561 |
| 2007/0055114 A1* | 3/2007 | Viertio-Oja et al. | 600/300 |
| 2007/0179399 A1* | 8/2007 | Viertio-Oja et al. | 600/559 |
| 2008/0194981 A1* | 8/2008 | Sarkela et al. | 600/544 |
| 2008/0234597 A1* | 9/2008 | Becker et al. | 600/544 |

OTHER PUBLICATIONS

Tononi, G. "An information integration theory of consciousness". BMC Neuroscience, 2004, 5:42.*
Alkire et al. "Consciousness and Anesthesia", Nov. 7, 2008 Science; 322(5903): 876-880.*
Casali, G. Adenauer, et al., General Indices to Characterize the Electrical Response of the Cerebral Cortex to TMS, pp. 1459-1468, vol. 49, Issue 2, Jan. 15, 2010, Elsevier, New York, NY, USA.

* cited by examiner

*Primary Examiner* — Navin Natnithithadha
*Assistant Examiner* — Etsub Berhanu
(74) *Attorney, Agent, or Firm* — Boyle Fredrickson, S.C.

(57) ABSTRACT

An evaluation of consciousness during the application of anesthetic evaluates causal propagation of neural activity in response to a localized stimulus, for example, by transcranial magnetic stimulation. A longer duration of invoked activity and a greater spatial dispersion of the invoked activity or greater complexity are matched to greater wakefulness comporting with a theory of consciousness as cortical integration of information moderated by intraneural communication.

8 Claims, 12 Drawing Sheets

METHOD FOR ASSESSING ANESTHETIZATION

CROSS-REFERENCE TO RELATED APPLICATIONS

This application claims priority from previously filed U.S. Provisional Patent Application Ser. No. 61/152,880 filed on Feb. 16, 2009 hereby incorporated by reference.

BACKGROUND OF THE INVENTION

The present invention relates generally to techniques for determining loss of consciousness during anesthetization and specifically to an objective measure of the effectiveness of anesthetization based on analysis of electroencephalographic signals.

Anesthetics are critical to modern surgical practice. Unfortunately, once in every 1000-2000 operations a patient may temporarily regain consciousness or even remain conscious during surgery. Such intraoperative awareness arises in part because of an inability to evaluate levels of consciousness.

Determining consciousness is difficult because of the different ways an anesthetic may work. For example, certain anesthetics may impair a person's willingness to respond even though they are conscious. Paralyzing agents, used to prevent unwanted movement during anesthesia, can also affect the patient's ability to respond to a command while the patient is conscious. It is possible that anesthetics which promote forgetfulness can cause a patient to fail to respond because they forget what to do before they can respond. Finally, some anesthetics promote profound amnesia, raising the possibility that retrospective oblivion is misinterpreted as loss of consciousness.

Anesthetics are thought to work by interacting with ion channels that regulate synaptic transmission and membrane potential in key regions of the brain and spinal cord and are known to affect electroencephalographic signals collected at the scalp. Prompted by this knowledge, brain function monitors have been developed to monitor EEG signals to determine levels of consciousness. Examples include the bispectral index (BIS) monitor manufactured by Aspect Medical Systems, Inc. of Newton, Mass. and the patient state index (PSI) monitor manufactured by Physiometrix of Billerica, Mass. both which employ proprietary algorithms to analyze EEG waveforms in order to output an index value indicating general levels of anesthesia. Although such devices may help guide anesthetic delivery, it is not clear whether they can indicate the presence or absence of consciousness, particularly near the transition point between these two states. Their limitations follow at least in part from an imperfect understanding of what consciousness is.

SUMMARY OF THE INVENTION

The present invention provides a method and apparatus for assessing loss of consciousness, for example, during anesthesia. While the inventors do not wish to be bound by a particular theory, it is hypothesized that loss of consciousness results from a loss of cortical integration caused by decreased communication between otherwise active neurons in different parts of the brain. The present invention assesses cortical integration by providing a neural stimulus through the use of transcranial magnetic stimulation, and monitoring the resulting neural activity. This activity may be characterized by the spatial propagation of the stimulation through the brain using at least two EEG electrodes, or by the temporal propagation of the stimulation through the brain using one or more electrodes, or by complexity of the resulting stimulation using as few as one electrode. In all cases, the response to stimulation is used to deduce cortical integration and thus consciousness.

Specifically, the present invention may provide an apparatus for assessing the consciousness using electroencephalographic sensors collecting electrical signals from firing neurons within a patient's brain and a neural stimulator using transcranial magnetic stimulation for promoting a localized excitation of neurons within the patient's brain at a location and time. An electronic computer receives the electrical signals from the electroencephalographic sensor and executes a stored program to (i) measure neural activity following the localized excitation of neurons by the neurostimulator; and (ii) output an indication of consciousness based on the measured propagation.

It is thus a feature of at least one embodiment of the invention to assess cortical integration through the use of an external stimulus and measured neural response to illuminate causal relationship between the activities of different sets of neurons.

The electronic computer may analyze the neural activity to determine how well the cortex is integrating information and where the output indication of consciousness is based on an assessment of information integration It is thus a feature of at least one embodiment of the invention to provide a theoretical underpinning for measurements of consciousness.

The neural activity may be analyzed to measure the complexity of the electrical signals and may map greater complexity to greater consciousness.

It is thus a feature of at least one embodiment of the invention to provide a consciousness measurement that may employ waveform analysis from as few as a single EEG electrode.

Alternatively or in addition the electronic computer may measure an extent of spatial propagation of excitation of neurons from the location of localized excitation and map greater spatial extent to greater consciousness.

It is thus a feature of at least one embodiment of the invention to measure a dimension of consciousness manifest in communication between widely separated cortical elements.

The measure of spatial propagation may sum distances between neural current sources and the point of localized excitation weighted by the values of neural current above a predetermined threshold.

It is thus a feature of at least one embodiment of the invention to provide a simple metric for spatial propagation.

Alternatively or in addition, the electronic computer may measure an extent of temporal propagation of excitation of neurons from the time of localized excitation and map greater temporal propagation to greater consciousness It is thus a feature of at least one embodiment of the invention to measure a dimension of consciousness manifest in prolonged communication between cortical elements.

The measure of temporal propagation may sum neural current sources above a predetermined threshold over all neurons.

It is thus a feature of at least one embodiment of the invention to provide a simple metric for temporal propagation. The electronic computer may calculate the extent of temporal propagation of excitation of neurons in two time periods and compare these calculations indicating greater consciousness to the extent that the decrease in temporal propagation between an initial and later time period is lower and a lesser consciousness to the extent that the decease in temporal propagation between the initial and later time period is higher.

It is thus a feature of at least one embodiment of the invention to provide a simple method of assessing absolute consciousness that is self-normalizing.

The two time periods may be before and after substantially 50 ms after the localized excitation of neurons by the neural stimulator.

It is thus a feature of at least one embodiment of the invention to permit a simple and rapid assessment of a state of consciousness.

The electronic computer measures both an extent of spatial and temporal propagation of excitation of neurons from the location and time of localized excitation, and the indication of consciousness may be a combination of the measures of spatial and temporal propagation.

It is thus a feature of at least one embodiment of the invention to provide a robust measure of consciousness combining possibly independent manifestations of consciousness.

Other features and advantages of the invention will become apparent to those skilled in the art upon review of the following detailed description, claims and drawings in which like numerals are used to designate like features.

DETAILED DESCRIPTION OF THE PREFERRED EMBODIMENT

Figure 1:
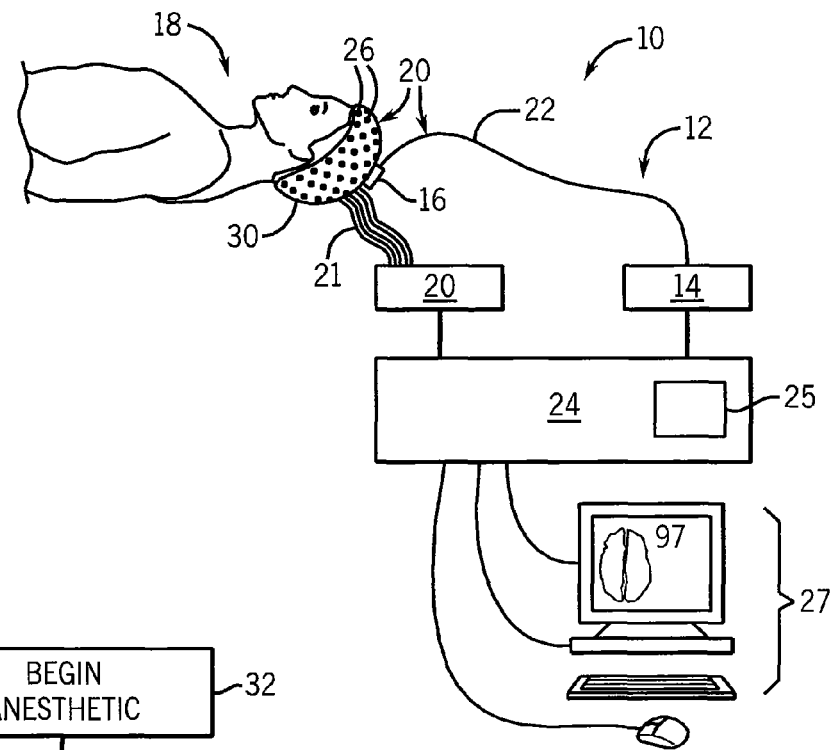
FIG. 1 is a simplified block diagram of a preferred embodiment of the present invention providing a transcranial magnetic stimulation (TMS) coil positionable on top of a patient's head and an electroencephalographic (EEG) system for detecting high-resolution EEG signals in response to a stimulation, both communicating with a controller executing a stored program.

Referring now to FIG. 1, an embodiment of the apparatus 10 of the present invention may use a transcranial magnetic stimulation (TMS) device 12 having a power unit 14 and a coil 16. During operation of the TMS device 12, a set of capacitors or other energy storage devices in the power unit 14 are charged and then rapidly connected to the coil 16 by leads 22 creating a monophasic or biphasic pulse of current in the coil 16 positioned at the top of the head of an anesthetized patient 18.

As is generally understood in the art, the pulse of current so produced causes a rapidly changing magnetic flux in the brain of the patient 18 which induces current within the brain tissue that stimulates neuron activity. The coil 16 may be a "butterfly coil", having windings in a figure-eight pattern to provide opposed magnetic flux in adjacent loops focusing the flux to a compact region. Other coils such as single loop coils and the like may also be used. TMS devices 12 suitable for use with the present invention are commercially available, for example, from Magstim of Whitland, South West Wales, United Kingdom.

The TMS device 12 may be controlled by a controller 24, for example an electronic computer executing a stored program 25, and could communicating with a user terminal 27 allowing for the output of a consciousness index value, as will be described, and other data and the input of commands according to methods well known and the art.

The controller 24 may also receive EEG signals from a high density EEG (hd-EEG) device 20. The EEG device 20 may provide standard EEG processing circuitry including amplifiers, gating circuitry and filters to provide for continuous EEG signals without disruption by the pulse produced by the TMS device 12. EEG devices 20 suitable for use with the present invention may be obtained from Nexstim of Helsinki, Finland under the trade name eXimia. The Nexstim device provides for a sample and hold amplifier that is specifically developed for use in monitoring EEG during TMS stimulation. It will be understood from the following descriptions, that hd-EEG will not be required in all situations and that for certain embodiments, for example, those relying solely or primarily on temporal propagation or waveform complexity, a single electrode may suffice, and further that as few as two electrodes may be used to deduce spatial propagation.

The EEG device 20 may receive signals over leads 21 from a set of electrodes 26 placed, for example, on the patient's scalp. Preferably, the high density EEG device provides in excess of 200 electrodes distributed over the scalp to provide for accurate spatial discrimination of neuron signals.

The electrodes 26 and the coil 16 of the TMS device 12 may be fitted to a cap 30 used to retain them in position on the head of the patient 18. The cap 30 may also provide for noise masking earplugs or earphones (not shown).

Figure 2:
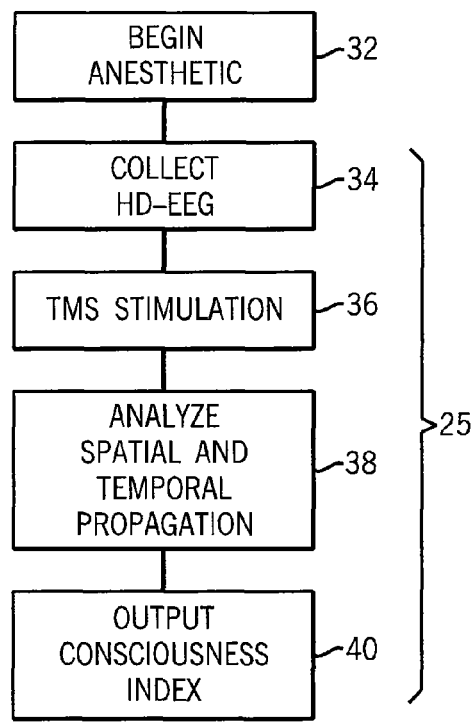
FIG. 2 is a block diagram showing the steps of the present invention executed in part by the controller.

Referring now to FIG. 2, the present apparatus may be used to assess consciousness during anesthetization of the patient as indicated by process block 32. During this process of applying the anesthetic, and optionally slightly preceding this time, the EEG device 20 may collect high-definition EEG signals as triggered by user input to the program 25 and as indicated by process block 34.

At periodic intervals during anesthetization or when the anesthesiologist believes a loss of consciousness has been obtained as indicated by an input to the program 25, a transcranial magnetic stimulation pulse may be applied as indicated by process block 36.

Immediately following each stimulation pulse, the controller 24 may analyze the time and location of the transcranial magnetic stimulation (the latter which may be known by placement of the coil 16 on the cap 30, data input by the user, or from analysis of the EEG signals themselves) to determine the spatial propagation of neural activity (indicating a spatial extent of neuron-to-neuron communication triggered by the localized stimulation), and/or the temporal propagation of neural activity (indicating the duration of neural activity triggered by the localized stimulation) as indicated by process block 38.

As indicated by process block 40, the propagation of neural activity may be analyzed, as will be described, to output, for example an index value indicating a degree of consciousness.

Figure 3A:
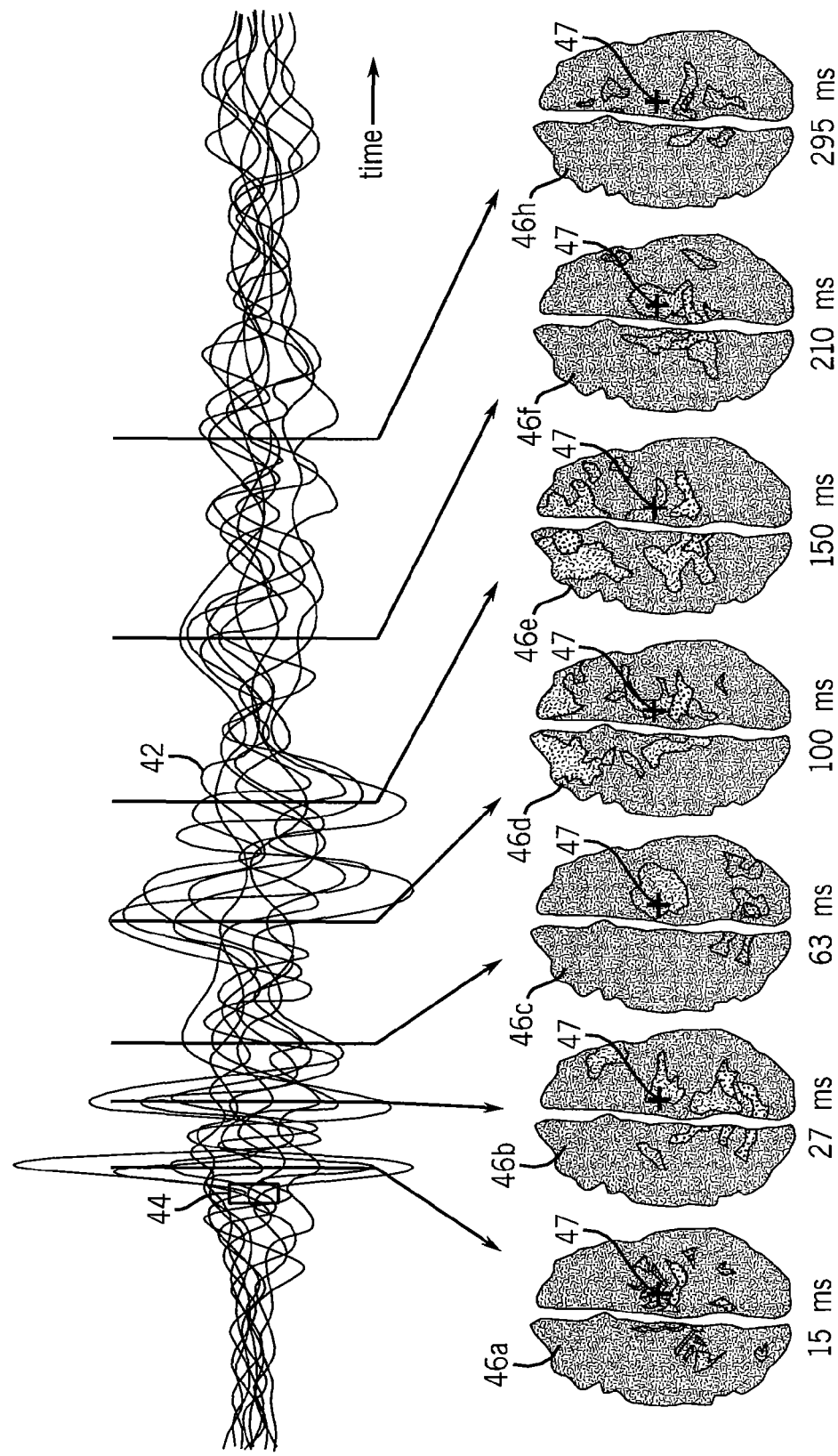
FIGS. 3a and 3b are each butterfly plots showing temporal propagation of the excitation provided by the TMS coil and brain maps showing spatial propagation of neural excitation, FIG. 3a showing a state of wakefulness and FIG. 3b showing a state of anesthesia.

Referring now to FIG. 3a, a butterfly plot 42 superimposing the TMS-evoked potential at all electrodes 26 shows the temporal progression of neural activity in a state of wakefulness after the TMS stimulation 44. Qualitatively, it can be seen that substantial induced neural activity continues in excess of 200 ms after the TMS stimulation 44.

Brain maps 46a-46h show the spatial locations of the invoked neural activity at 15 ms, 27 ms, 63 ms, 100 ms, 150 ms, 210 ms, and 295 ms after the stimulation 44. Qualitatively, the propagation of neural activity from the site of the stimulation 47 shows substantial spatial spreading of the excitation to more distant cortical areas.

Figure 3B:
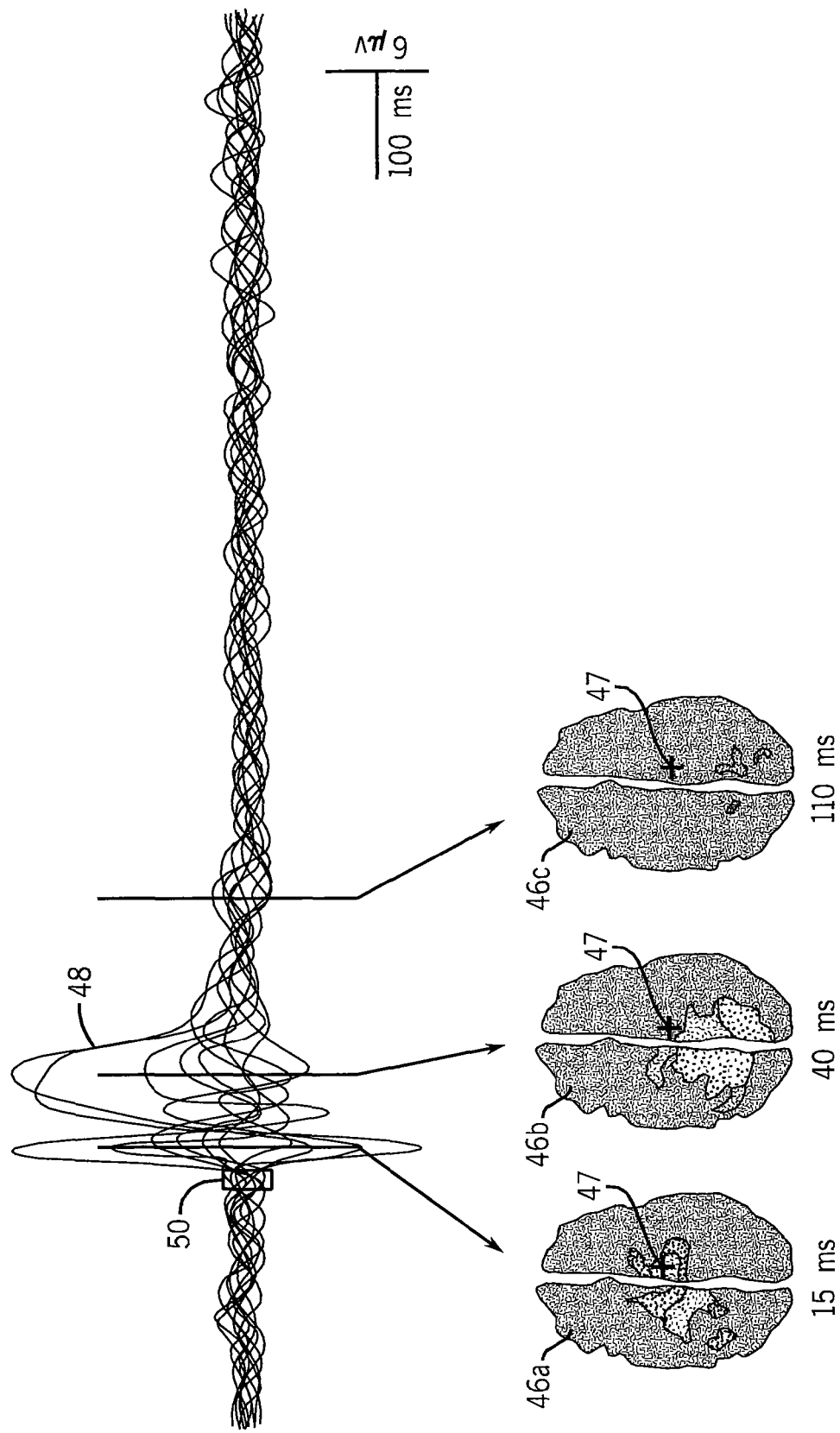

A similar diagram is shown in FIG. 3b for a state of anesthesia. Again, a butterfly plot 48 superimposes TMS invoked potential at all electrodes 26 to display a temporal progression of neural activity. Brain maps 46a-46c show the spatial locations of invoked neural activity at 15 ms, 40 ms, and 110 ms. In this case, induced neural activity after the transcranial stimulation 50 has essentially settled by 110 ms after the stimulation 44 and qualitatively there appears to be little or no invoked neural activity any substantial distance from the site of the stimulation 47.

A useful metric for quantitative characterization of temporal propagation of the invoked neural activity is through the use of the measure of significant current density (SCD), and a useful method for quantitative characterization of spatial propagation of the invoked neural activity is through the use of the measure of significant current scatter (SCS). Generally, SCD evaluates neural activity against a threshold and then sums that activity for each point in time over the entire brain (or measurement region of the EEG device 20) thus providing a global estimate of neural activity. Generally, SCS sums neural activity above a threshold as weighted by its distance from the stimulation 47 thus providing a measure of the spatial spreading of the invoked neural activity. The details of this methodology are described in: "General Indices to Characterize Electrical Response of the Cerebral Cortex to TMS", Casali A G, Casarotto S, Rosanova M, Mariotti M, Massimini M (2010) Neuroimage 49(2): 1459-1468, hereby incorporated by reference. The particular metrics of SCS and SCD, of course, are only examples of many possible mathematical techniques that can be used to quantify spatial and temporal propagation of EEG signals, and the invention should not be considered limited to these particular mathematical formulations. Further, temporal and spatial propagation of EEG signals are but two possible measures of integrated information Φ in the brain, discussed further below. Other measures may look at EEG complexity or the like.

Referring now to FIG. 45, this difference in spatial and temporal propagation of invoked activity can be seen in the time course of currents in Broadman areas 6 (BA 8) near the point of stimulation in the pre-motor cortex and Broadman area 8 (BA 8) in the anterior cortical area expressed in terms of SCD. As can be seen, the SCD for the wakeful state (shown in the left side of FIG. 4) retains higher values both close to and far from the site of stimulation 47 during a time period from zero to 500 ms after the TMS stimulation 44. In contrast, in state of anesthesia (shown in the right side of FIG. 4), the SCD drops abruptly in time and in space although it exhibits a higher peak proximate to the site of stimulation 47 shortly after the stimulation.

Referring now to FIGS. 5a-5g, SCD and SCS were measured in multiple experiments 59 for wakefulness 60 and anesthesia 62 following a transcranial magnetic stimulation of the pre-motor cortex at time zero, each providing data for wakefulness 60 and for anesthesia 62. The data is displayed in time plots 57 and bar charts 64, the latter providing the mean SCD or SCS for each of the wakefulness and anesthesia states over the entire post-stimulation period.

Figure 6:
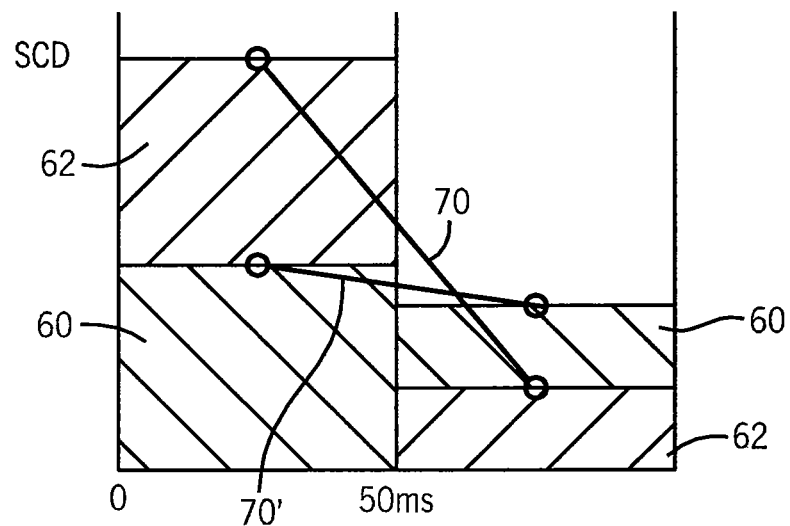
FIG. 6 is a bar chart showing change in mean SCD for wakefulness and anesthesia in two intervals divided at 50 ms after stimulation.

Referring now to FIG. 6, this data may be used to construct an index indicating consciousness that may be output to guide, for example, anesthetization. Generally the index will map greater spatial propagation and greater temporal propagation to greater consciousness. In one embodiment, the index may obtain mean SCD values in two time periods, for example, from zero to 50 ms and from 50 ms to 500 ms after stimulation. A difference value or slope of the line 70 may then be used to provide a quantitative measurement of consciousness with lines 70 having higher slope indicating greater consciousness and lines 70' having lesser slope indicating lesser consciousness. By using the slope or difference, such a measurement is self-normalizing with respect to possibly different sensitivities of the EEG electrodes.

Figure 7:
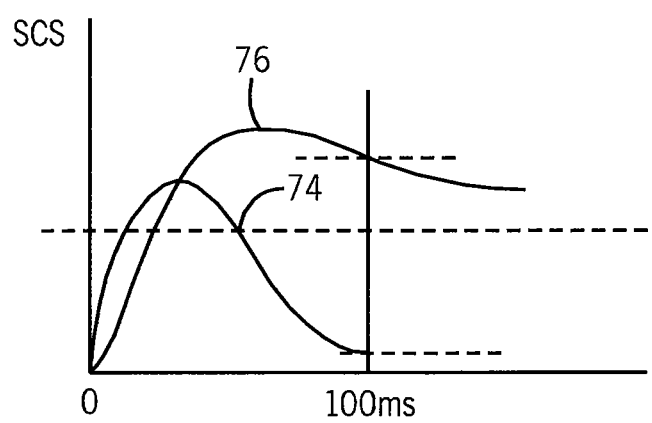
FIG. 7 is a time plot of SCS analyzed at 100 ms after stimulation.

Alternatively and referring to FIG. 7, SCS may be measured and evaluated at a fixed time period after the stimulation (set to time zero). In general, SCS 76 during consciousness will be substantially above baseline for more than 200 ms while SCS 74 during loss of consciousness will return to baseline within approximately 100 ms from the stimulation. Accordingly, measurement of SCS at 100 ms compared to baseline can be used to provide a quantitative indication of consciousness output to the user.

Generally an index can be prepared by using either or both of these measures of SCD and/or SCS by combining them with appropriate weighting in a single index which may be normalized, for example, to a scale from zero to 100 with zero indicating loss of consciousness and 100 indicating full consciousness.

In an alternative embodiment or in combination with the above techniques, the invention may assess the "complexity" of the EEG signal after neural stimulation. This approach may permit consciousness measurements with a single or small number of EEG electrodes. A variety of different measures of complexity may be possible including, for example, multi-scale entropy, Lempel-Ziv complexity or the like. In a variation on this approach, waveforms for successive different neural stimulations, for example, implemented with successive slight movements or rotations of the TMS coil, can be compared to assess greater or lesser variation in the EEG signals, greater variation suggesting a greater level of consciousness.

Example I

While the inventors do not wish to be bound by particular theory, unlike other consciousness measurement systems currently available in the market, the present invention is based on a theoretical underpinning linking consciousness to integrated information Φ, the latter related to the repertoire of different states (information) that can be discriminated by the brain as a whole (integration). Integrated information attempts to quantify the information generated when the brain enters one particular state in its repertoire, above and beyond the information generated independently by its parts. See generally, G. Tononi, BMC Neurosci. 5, 42 (2004). While integrated information cannot be measured directly except in extremely simple systems, the present invention assesses integrated information using the propagation of neural activity from a stimulus as a proxy for the communication between different functionally-specific areas of the brain when information is integrated, or by using the complexity of the waveform after a single or multiple varying stimulations, this complexity suggesting a greater repertoire of states associated with greater integration. See also, Consciousness and Anesthesia, M T Alkire, A G Hudetz, G Tononi, Science, vol. 322. No. 5903, pp. 876-880 (2008).

The data of FIGS. 5a-5g was collected from six subjects who received intravenous midazolam at doses up to 0.2 mg/kg. An "observer's assessment of alertness/sedation" (OAA/S) scores of "1" (unresponsive to verbal and mild physical stimulus) was reached for a sufficient period of time that hd-EEG responses to TMS could be measured. No subjects experienced respiratory depression (18±1.4 per min pre-induction; 16±4 per min post-induction), desaturation (minimum SaO2 95%), or physiologically meaningful changes in heart rate (59±7 per min pre-induction; 69±12 per min post-induction) or blood pressure (systolic: 127±15 mm Hg pre-induction; 113±10 mm Hg post-induction; diastolic: 74±9 mm Hg pre-induction; 62±5 mm Hg post-induction). Subjects also displayed no spontaneous/voluntary behavior during TMS/hd-EEG sessions performed at level 1 OAA/S, and regained full consciousness (level 5 OAA/S) within 100 minutes on average (range 42-158 minutes).

In debriefing sessions during the recovery period subjects reported no subjective experience during loss of consciousness (LOC). By contrast, subjects interrogated while transitioning into LOC (level 3 OAA/S) reported a sensation of light-headedness, mild euphoria, and well-being.

Compared to wakefulness, we found a marked change in TMS-evoked brain responses during midazolam induced LOC. Before the injection of the anesthetic (level 5 alertness, OAA/S), TMS pulses to premotor cortex evoked a complex spatio-temporal pattern of low-amplitude, fast-frequency scalp waves, as shown by the average TMS-evoked EEG potentials recorded at all electrodes and superimposed in a butterfly plot (butterfly plot 42 in FIG. 3a shows data from one subject). Conversely, following midazolam-induced LOC (level 1 OAA/S), TMS pulses gave rise to high-amplitude, low-frequency EEG voltages, which faded shortly after the stimulation (butterfly plot 48 in FIG. 3b shows data from one subject).

To further explore the neural events underlying these EEG patterns, we calculated the currents evoked by TMS in the cortex before and after LOC. Before LOC, TMS-evoked cortical currents lasted for at least 300 ms following the stimulation, and shifted among cortical areas distant from the TMS-targeted brain area (brain maps 46a-46h in FIG. 3a). By contrast, TMS-evoked cortical currents after LOC faded within 150 ms and remained more localized to the stimulated site (brain maps 46a-46c in FIG. 3b).

Figure 4:
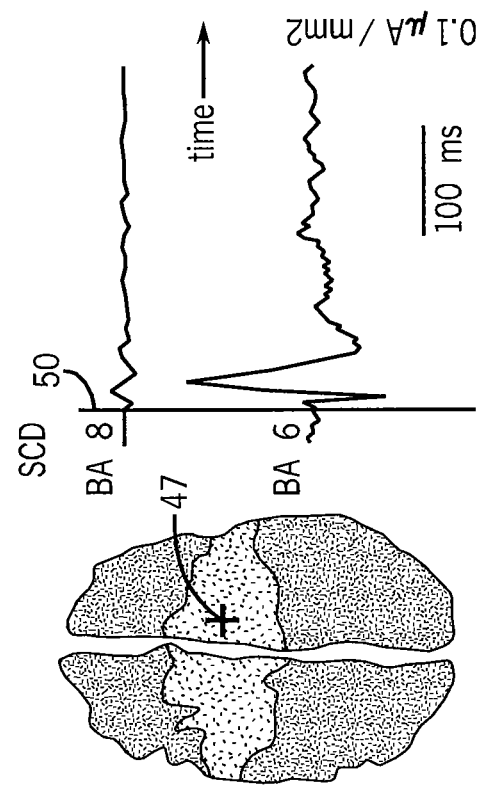
FIG. 4 is a pair of brain maps showing cortical currents invoked by stimulation of the pre-motor cortex as plotted for the Broadman areas 6 (premotor cortex) and Broadman areas 8 (anterior cortical area) showing a difference between wakefulness (left brain map) and anesthesia (right brain map)
Figure 4:
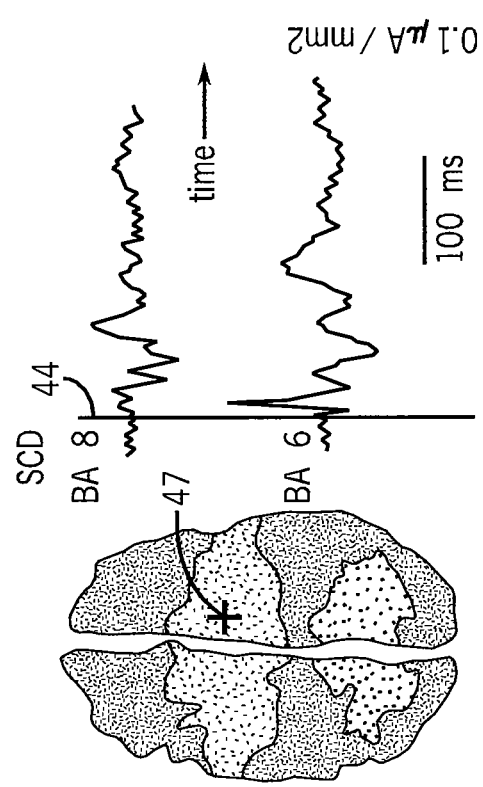
Figure 5A:
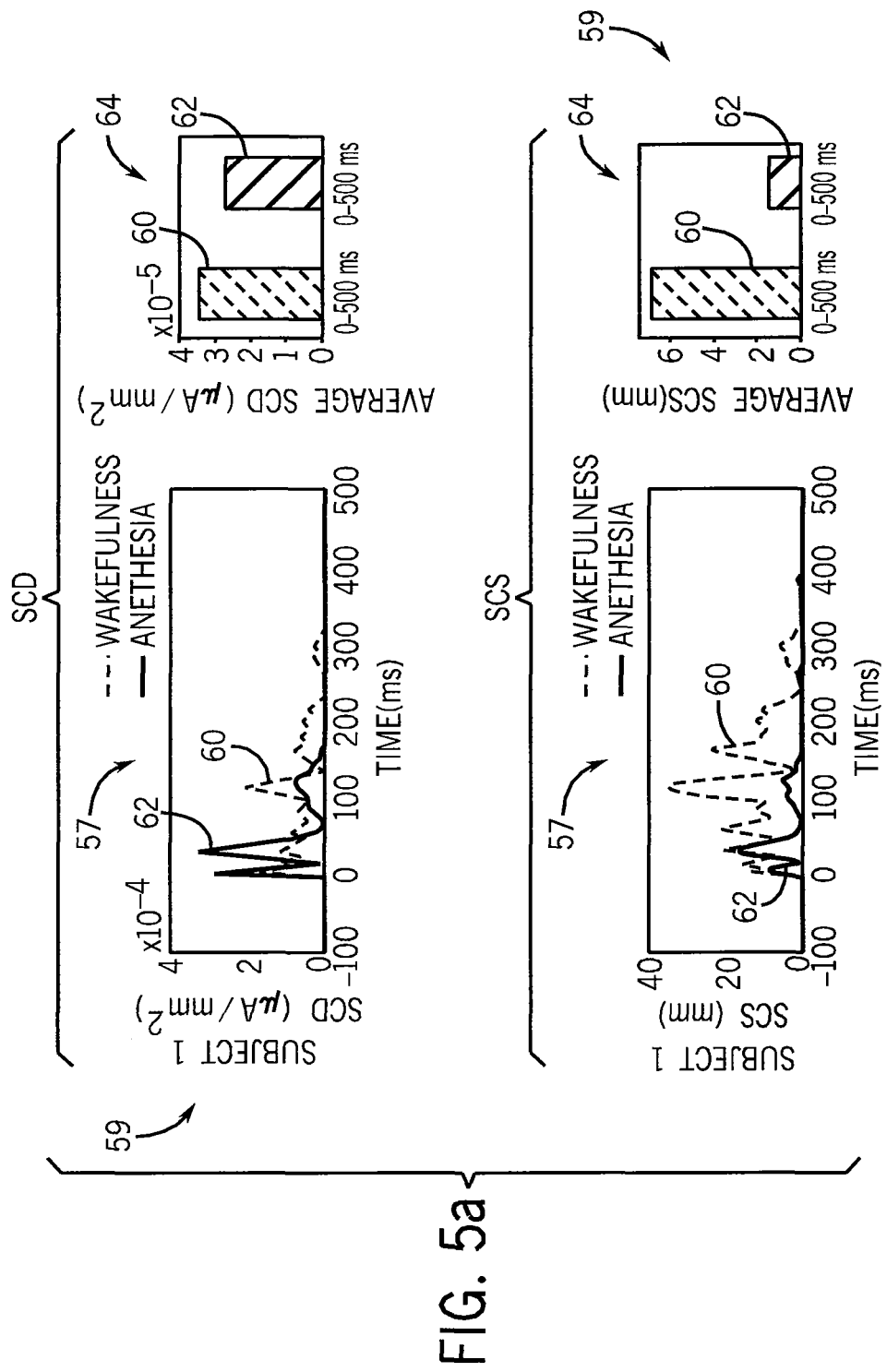
FIG. 5a-5g are a set of chart pairs, the right side of the top row showing time plots of significant current density (SCD) in wakefulness and anesthesia over time and the left side of the top row showing of a bar chart of mean SCD over the entire time interval after the neural stimulation, and the left side of the bottom row showing a time plot of significant current scatter (SCS) in wakefulness and anesthesia over time and the right side of the bottom row showing a bar chart of SCS over the entire interval after neural stimulation, for individual experiments and an average of the experiments separated by rows.
Figure 5B:
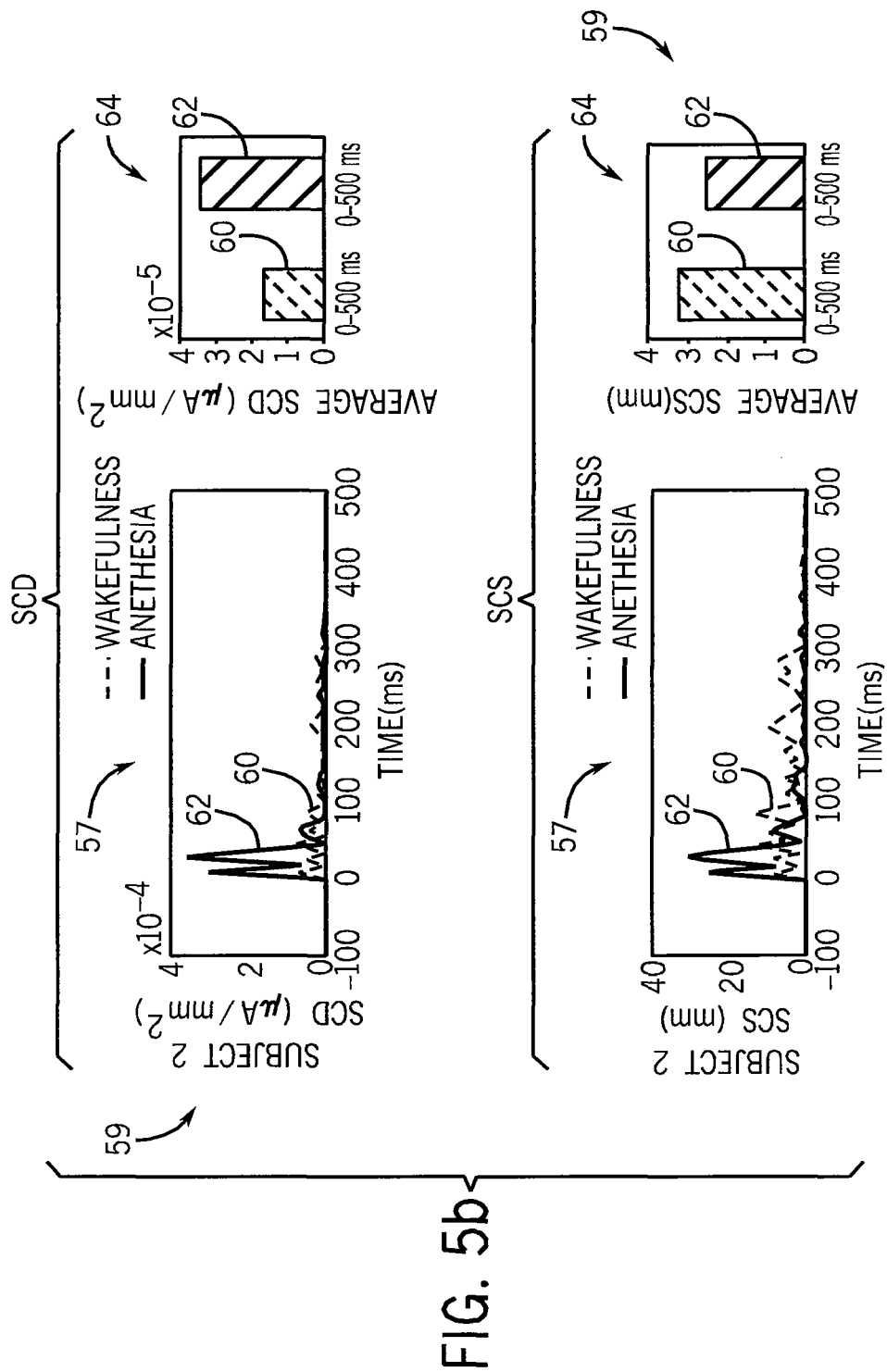
Figure 5C:
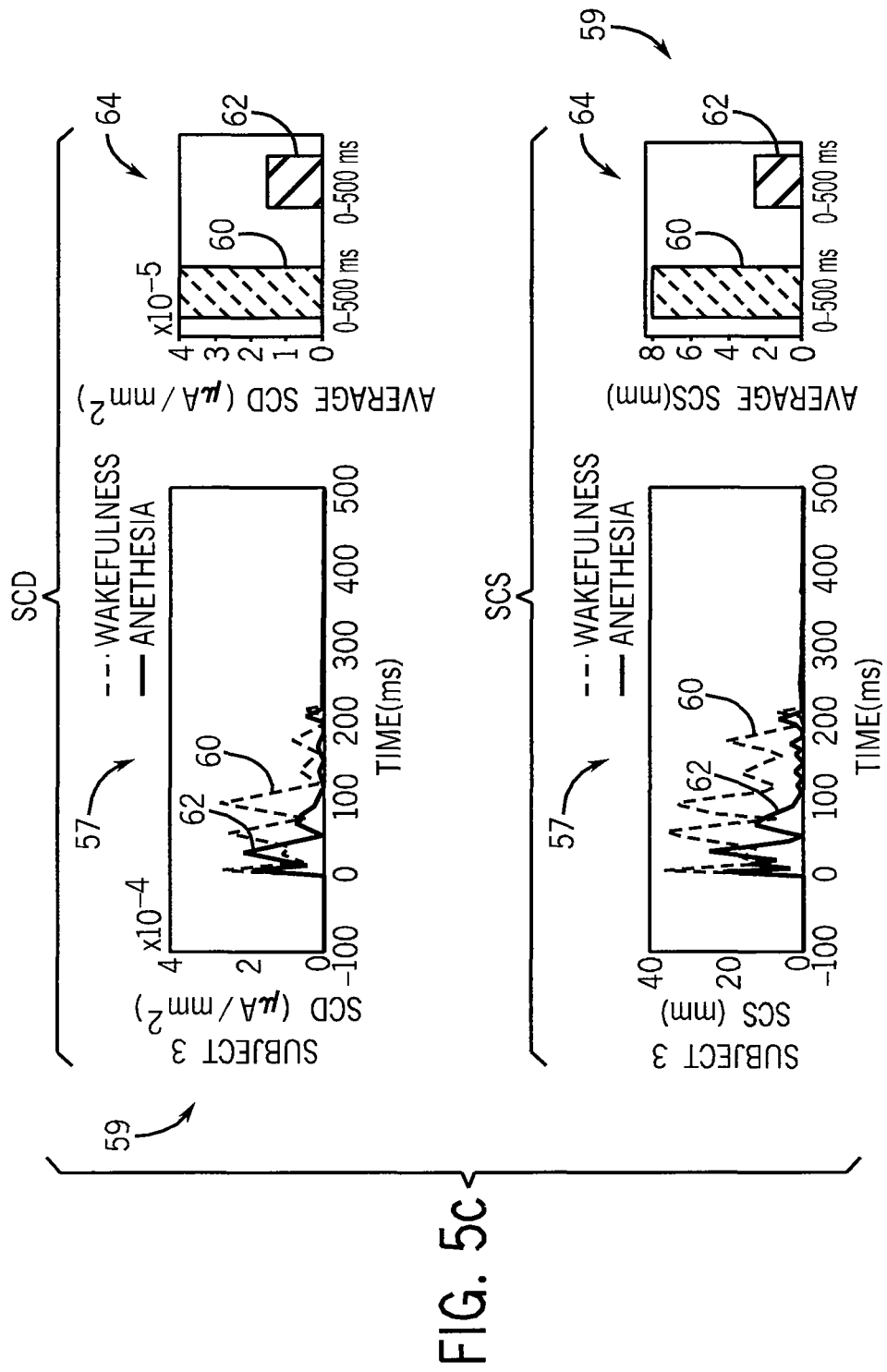
Figure 5D:
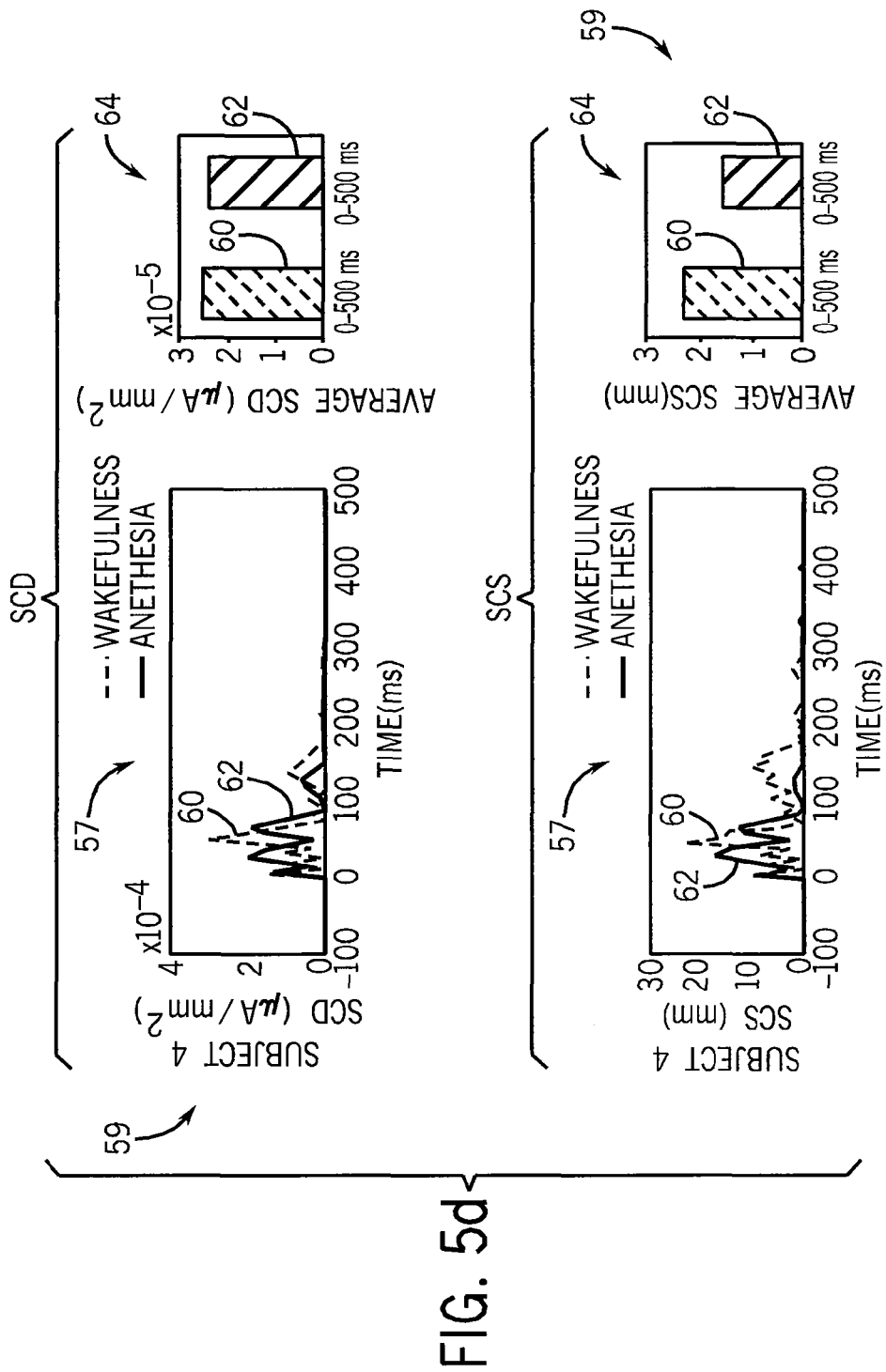
Figure 5E:
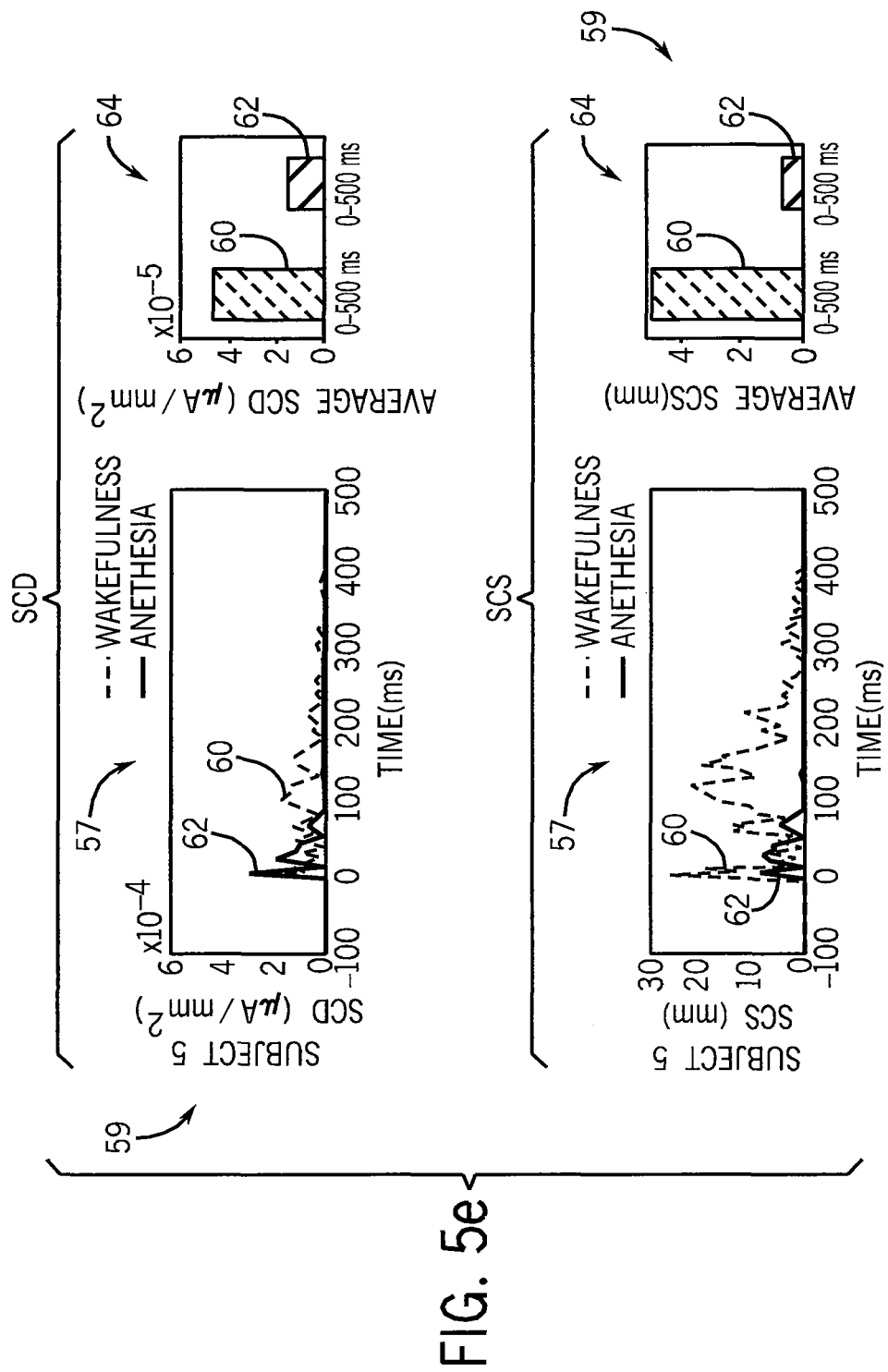
Figure 5F:
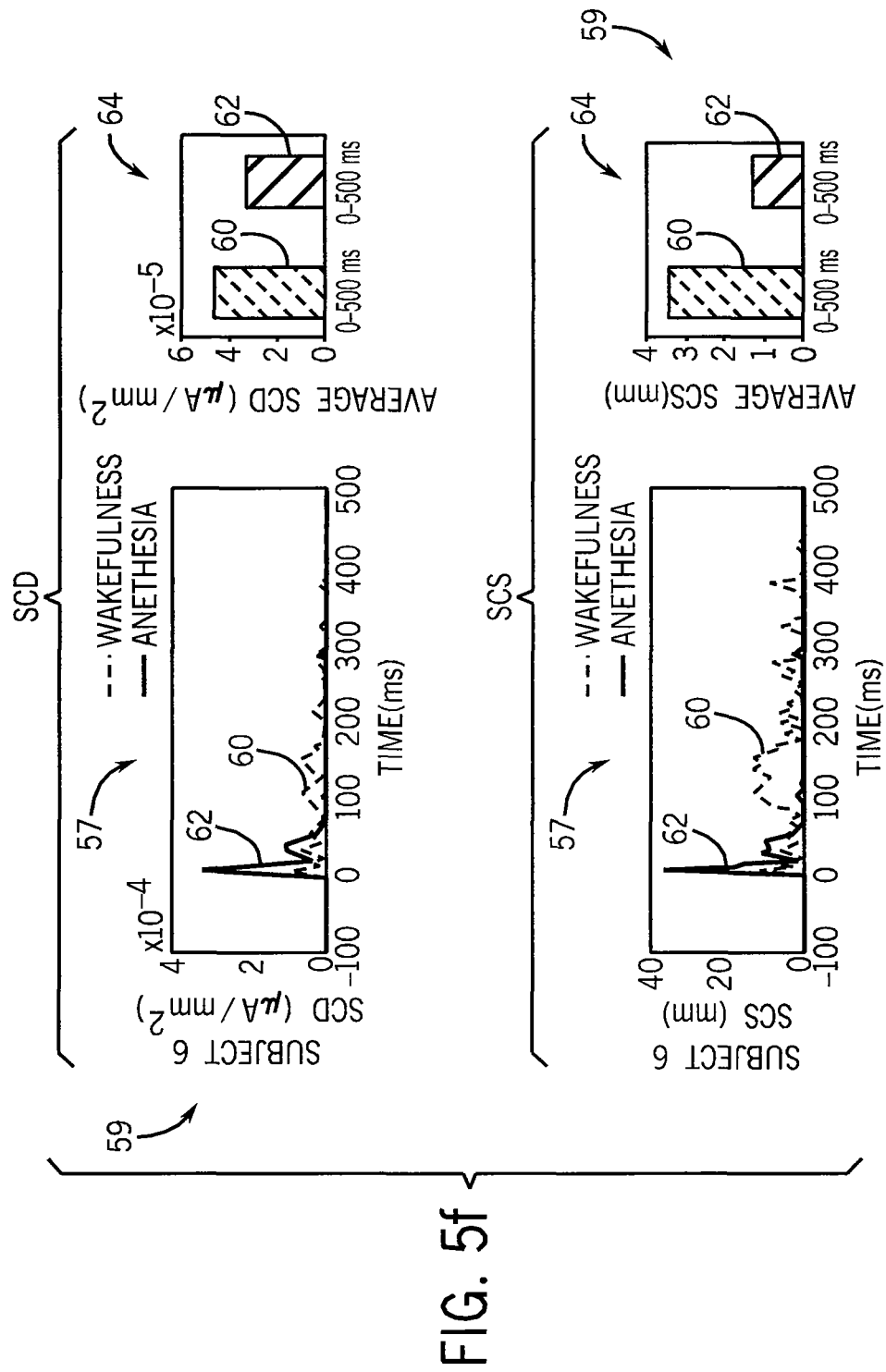
Figure 5G:
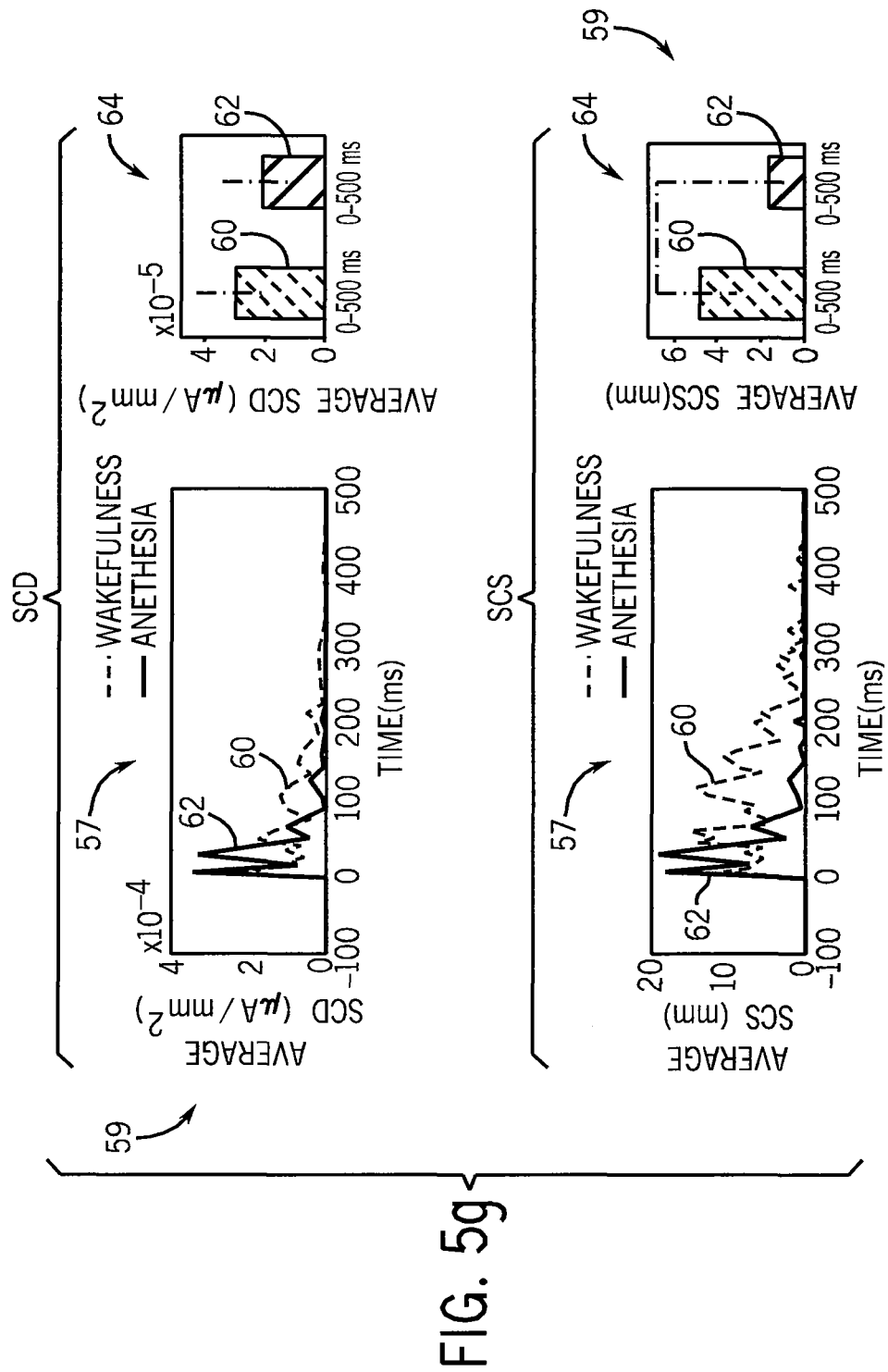

In order to capture the pattern of spatial activation in the two conditions, TMS-evoked cortical currents were cumulated for the entire post-stimulus interval and displayed topographically for both conditions (See FIG. 4). While the activity evoked by TMS at the stimulation site, the premotor cortex (BA 6), was similar across conditions, its time course was markedly different. During wakefulness, the immediate response to TMS consisted of fast-frequency oscillations. By contrast, during anesthesia, TMS evoked responses were slower in frequency though the initial component was of higher amplitude, consisting of a large positive wave followed by a negative deflection. This local response was found in all subjects during LOC. In one subject, in which TMS-evoked cortical activity was recorded at an intermediate level of sedation (level 3 OAA/S), single trial analysis showed that this large positive-negative wave took shape gradually while transitioning from wakefulness (level 5) to deep sedation (level 1). Specifically, while the positive peak of the TMS-evoked wave first appeared at level 3 of sedation, the positive-negative sequence was fully established only when reaching level 1. This initial, stronger response during LOC remained largely restricted to the premotor cortices, and affected only marginally the activity of other cortical areas. This breakdown of cortico-cortical effective connectivity was also evident when inspecting the time courses of the TMS-evoked cortical currents. For instance, the time course of cortical currents in BA 8 (prefrontal cortex) that is anatomically connected to BA 6 (premotor cortex) was not affected by the strong activation evoked by TMS in the premotor cortex.

To quantify changes in strength (activity) and propagation (connectivity) of TMS-evoked cortical responses during LOC, two recently developed indexes, significant current density (SCD) and significant current scattering (SCS), were calculated for each subject in wakefulness and anesthesia. SCD was computed by cumulating in space the statistically significant cortical currents evoked by TMS (FIGS. 5a-5g, left column). The time course of SCD revealed that, in each subject, the initial TMS-evoked cortical activity, related to the large positive-negative wave, was higher in the anesthesia condition, whereas subsequent cortical activity was stronger during wakefulness. When cumulating SCD in two post-TMS time ranges, 0-50 and 50-500 ms, we found that in the 0-50 ms interval SCD was significantly higher during anesthesia ($p=0.016$, Mann Whitney), whereas in the 50-500 ms range SCD was significantly higher during wakefulness ($p=0.016$, Mann Whitney). The average SCD in the entire post-stimulus interval was reduced during anesthesia, indicating a diminished response to the TMS, though the two conditions differed only at trend level ($p=0.1$, Mann Whitney).

By contrast SCS, computed by measuring the geodesic distance between any significant current source and the site of stimulation, discriminated effectively between the two conditions (FIGS. 5a-5g, right column). Specifically, in each subject, mean SCS was significantly higher in wakefulness compared to anesthesia ($p=0.009$, Mann Whitney). Furthermore, the time course of SCS showed that, in each subject, SCS during wakefulness was significantly increased compared to baseline for more than 200 ms, while during anesthesia SCS returned to baseline within 100 ms from TMS.

While the present invention has been described in the context of assessing anesthesia through measurement of consciousness, it will be understood that it is generally applicable to a variety of consciousness measuring situations, for example, assessing consciousness in a patient in a vegetative state and/or minimally conscious state, and assessing consciousness in other medical circumstances unrelated anesthesia.

When the invention is used to assess consciousness during anesthesia, the consciousness metric output may be used to adjust the delivery of the anesthesia to ensure an appropriate loss of consciousness with minimum dosage during the course of the medical procedure.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

I claim:

1. An apparatus for assessing consciousness comprising:
   an electroencephalographic sensor for collecting electrical signals from firing neurons within a patient's brain;
   a neural stimulator for promoting a localized excitation of neurons within the patient's brain at a location and time using transcranial magnetic stimulation; and
   an electronic computer for receiving the electrical signals from the electroencephalographic sensor and executing a stored program to:
   (i) measure neural activity indicated by the electrical signals following the localized excitation of neurons by the neural stimulation,
   (ii) analyze the neural activity to determine how well the patient's brain is integrating information by evaluating spatial propagation of excitation of neurons, and
   (iii) provide an indication of consciousness is based on an assessment of information integration; and
      wherein the electronic computer is configured to measure an extent of the spatial propagation of excitation of neurons from a location of localized excitation by evaluating a combination of strength and location of neural current sources over multiple locations within the brain and map greater spatial propagation to greater consciousness.

2. An apparatus for assessing consciousness comprising:
   an electroencephalographic sensor for collecting electrical signals from firing neurons within a patient's brain;
   a neural stimulator for promoting a localized excitation of neurons within the patient's brain at a location and time using transcranial magnetic stimulation; and
   an electronic computer for receiving the electrical signals from the electroencephalographic sensor and executing a stored program to:
   (i) measure neural activity indicated by the electrical signals following the localized excitation of neurons by the neural stimulation,
   (ii) analyze the neural activity to determine how well the patient's brain is integrating information, and
   (iii) provide an indication of consciousness is based on an assessment of information integration; and
   wherein the electronic computer is configured to
      measure a temporal propagation of the excitation of neurons from the time of localized excitation,
      map greater temporal propagation to greater consciousness, and
      measure an extent of temporal propagation of excitation of neurons by summing neural current sources above a predetermined threshold over all neurons.

3. The apparatus of claim 2 wherein the electronic computer is configured to calculate the extent of temporal propagation of excitation of neurons in two time periods in determining the indication of consciousness and compares these calculations indicating greater consciousness to the extent that the temporal propagation in a latter time period is higher and less consciousness to the extent that the temporal propagation in an earlier time period is higher.

4. The apparatus of claim 3 wherein the two time periods are before and after substantially 50 ms after the localized excitation of neurons by the neural stimulator.

5. The apparatus of claim 2 wherein the electronic computer is configured to also measure an extent of spatial propagation of excitation of neurons from the location of localized excitation by evaluating a combination of strength and location of neural current sources over multiple locations within the brain and map greater spatial extent to greater consciousness; and
   wherein the indication of consciousness is a combination of the measures of spatial and temporal propagation.

6. A method of assessing consciousness during anesthetization comprising the steps of:
   (a) applying an anesthetic to a patient;
   (b) applying a neural stimulation to a patient's brain for promoting a localized excitation of neurons within the patient's brain at a location and time using transcranial magnetic stimulation;
   (c) collecting electrical signals from firing neurons within a patient's brain; and
   (d) using an electronic computer, receiving the electrical signals to measure neural activity following the localized excitation of neurons by neural stimulation, wherein measuring neural activity following the localized excitation of neurons by neural stimulation includes:
      measuring an extent of spatial propagation of excitation of neurons from a location of localized excitation by evaluating a combination of strength and location of neural current sources over multiple locations within the brain, and
      mapping greater spatial propagation to greater consciousness;
   (e) analyzing the measured neural activity to assess how well the patient's brain is integrating information; and
   (f) outputting from the electronic computer an indication of consciousness based on how well the patient's brain is integrating information.

7. The method of claim 6 wherein the anesthetic is midazolam.

8. The method of claim 6 wherein measuring neural activity also includes measuring temporal propagation of the excitation of neurons from a time of localized excitation, mapping greater temporal propagation to greater consciousness, and measuring an extent of temporal propagation of excitation of neurons by summing neural current sources above a predetermined threshold over all neurons.

* * * * *